United States Patent [19]

Sekioka et al.

[11] Patent Number: 4,465,503

[45] Date of Patent: Aug. 14, 1984

[54] DIPHENYL ETHER DERIVATIVES, PROCESS FOR PREPARING THE SAME AND HERBICIDAL COMPOSITIONS CONTAINING THE SAME

[75] Inventors: Hakobu Sekioka; Mitsuaki Takenaka; Yoshio Kawaguchi; Seiji Takamura; Minoru Nishimura; Masanori Watanabe, all of Ube, Japan

[73] Assignee: Ube Industries Ltd., Ube, Japan

[21] Appl. No.: 173,732

[22] Filed: Jul. 30, 1980

[30] Foreign Application Priority Data

Aug. 7, 1979 [JP] Japan ............................. 54-99914
Oct. 12, 1979 [JP] Japan ............................. 54-130870

[51] Int. Cl.$^3$ ............................. A01N 43/32; C07D 317/04
[52] U.S. Cl. ............................. 71/88; 549/372; 549/373; 549/451
[58] Field of Search ............................. 71/88; 260/340.7; 549/372, 373, 451

[56] References Cited

U.S. PATENT DOCUMENTS

| | | | |
|---|---|---|---|
| 3,419,620 | 12/1968 | Becher et al. | 71/88 X |
| 4,053,297 | 10/1977 | Riehter | 71/88 |
| 4,093,446 | 6/1978 | Bayer et al. | 71/88 X |
| 4,097,581 | 6/1978 | Faroog et al. | 71/88 X |
| 4,227,914 | 10/1980 | Fory et al. | 71/88 X |
| 4,293,329 | 10/1981 | Grove | 549/451 |

FOREIGN PATENT DOCUMENTS 2739067 3/1978 Fed. Rep. of Germany .

*Primary Examiner*—Catherine L. Mills
*Attorney, Agent, or Firm*—Frishauf, Holtz, Goodman & Woodward

[57] ABSTRACT

There are presented new diphenyl ether derivatives having a substituent selected from a halogen atom, a trifluoromethyl group and a methoxy group at the 4-position in one phenyl moiety, having optionally also halo-substituents at the 2- and 6-positions, and having a nitro group at the 4'-position and a substituent selected from an unsubstituted or substituted (1,3-dioxorane-4-yl)methoxy group, an unsubstituted or substituted (1,3-dioxa-5-cyclohexyloxy) group and an alkyl- or (substituted)amino-sulfonyloxy group at the 3'-position in the other phenyl moiety. They exhibit improved herbicidal effects on various weeds without any adverse phytotoxic effect on crops, e.g. rice seedlings.

14 Claims, No Drawings

DIPHENYL ETHER DERIVATIVES, PROCESS FOR PREPARING THE SAME AND HERBICIDAL COMPOSITIONS CONTAINING THE SAME

This invention relates to a new group of diphenyl ether derivatives, to a process for preparing the same and also to the new use of the said diphenyl ether derivatives as a herbicide.

There have been heretofore proposed a wide variety of diphenyl ether derivatives as agricultural herbicides and a considerable number of them has been on the market for practical use: For example, such herbicides as "NIP" (active ingredient: 2',4'-dichloro-4-nitrodiphenyl ether), "CNP" (active ingredient: 2',4',6'-trichloro-4-nitrodiphenyl ether) and "TOPE" (active ingredient: 3'-methyl-4-nitrodiphenyl ether) may be mentioned. These previously known diphenyl ether type herbicides can generally show a superior herbicidal effect in soil treatment against annual weeds of the family Gramineae developed in a paddy field, but they have a common characteristic of having an inferior herbicidal effect against various weeds in foliar treatment or annual broad-leaved weeds and perennial weeds and having disadvantageous phytotoxic effects on transplanted rice seedlings such as brown discoloration of leaf sheath, floating of leaf and inhibition of tillering. Further, it can be frequently seen in those derivatives of such a type that it may unexpectedly be different, upon differences in their chemical structures such as those in the sort, number or position of substituents, whether a herbicidal effect may be exerted, how high a herbicidal effect may be, how rapidly a herbicidal effect may be developed or how a phytotoxicity may be to crops and so on.

It is, accordingly, a primary object of this invention to provide new diphenyl ether derivatives which show an excellent herbicidal effect.

Another object of this invention is to provide a process for preparing the above-mentioned new diphenyl ether derivatives.

A further object of this invention is to provide a herbicidal compositions which comprises as an active ingredient at least one of the new diphenyl ether derivatives as mentioned above.

According to the present invention, there is provided a novel diphenyl ether derivative represented by the formula (I):

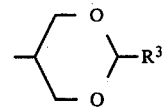
(I)

wherein X and Z each represent a hydrogen atom or a halogen atom; Y represents a halogen atom, a trifluoromethyl group or a methoxy group; and R represents a group of the formula:

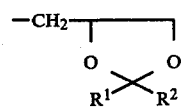

(wherein each of $R^1$ and $R^2$ is a lower alkyl group, a hydrogen atom or a chloromethyl group, or $R^1$ and $R^2$ taken together may form a saturated alicyclic ring), a group of the formula:

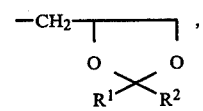

(wherein $R^3$ is hydrogen atom or a methyl group) or a group of the formula: $-SO_2R^4$ (wherein $R^4$ is a lower alkyl group, a mono- or di-loweralkylamino group or a monochloromethyl group).

The diphenyl ether derivatives (I) of this invention can show a superior weed-killing activity by pre- and post-emergence treatment in soil; in other words, they have both soil treating activities and foliar treating activities. Then, they are effective against various weeds such as annual or perennial weeds of the family Gramineae growing in a paddy or upland field, broadleaved weeds and the like.

Accordingly, the herbicidal diphenyl ether derivatives (I) of this invention can be effectively applied to a paddy field as a pre-emergent herbicide before or after rice planting or a post-emergent herbicide against perennial weeds or broad-leaved weeds after 1-2 weeks from rice planting, and, further, they can be effectively employed as a soil treatment herbicide before or after sowing in an upland field or as a foliar treatment herbicide against various weeds in an orchard, a tea garden, a mulberry field or a non-crop land. In addition, the diphenyl ether derivatives (I) of this invention has a particular characteristic that they exert no phytotoxic effects on rice seedlings such as brown discoloration of leaf sheath, floating of leaf and inhibition of tillering, without any phytotoxicity to other crops and toxicity to human beings and domestic animals as well as fish and shellfishes, and do not have any other harmful properties such as a nasty smell and the like.

Referring now to preferable classes of compounds represented by the above formula (I), the group represented by Y may preferably a trifluoromethyl group or a halogen atom. When Y is a trifluoromethyl group, X may preferably a halogen atom and Z a hydrogen atom. When Y is a halogen atom, X and/or Z may preferably a halogen atom. In the group represented by the formula:

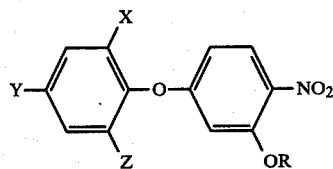

the lower alkyl group represeted by $R^1$ and $R^2$ may preferably have 1 to 4 carbon atoms. When $R^1$ and $R^2$ are bonded to each other to form a saturated alicyclic ring, there can generally be formed a 4- to 7-membered ring, typically a 5-membered ring. As the groups represented by $R^1$ and $R^2$, hydrogen atoms are most preferred. In the group represented by the formula

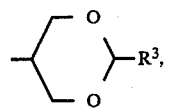

$R^3$ may preferably be a hydrogen atom. When the group R in the formula (I) is a group of the formula —$SO_2R^4$, the lower alkyl moiety in the group $R^4$ may preferably have 1 to 4 carbon atoms.

Typical examples of the diphenyl ether derivatives (I) are given in the following Table 1 for illustrating purpose only.

TABLE 1

| Compd. No. | Chemical Structure | Physical Properties |
|---|---|---|
| 1 | Br—C₆H₄—O—C₆H₃(NO₂)—OCH₂—[2,2-spiro-1,3-dioxolane/cyclopentane] | m.p. 71–74° C. |
| 2 | 2,4-Cl₂—C₆H₃—O—C₆H₃(NO₂)—OCH₂—[spiro dioxolane] | $n_D^{24.7}$ 1.5863 |
| 3 | 2-Br-4-Cl—C₆H₃—O—C₆H₃(NO₂)—OCH₂—[spiro dioxolane] | $n_D^{25.5}$ 1.5835 |
| 4 | 2-Cl-4-Br—C₆H₃—O—C₆H₃(NO₂)—OCH₂—[spiro dioxolane] | $n_D^{26.5}$ 1.5936 |
| 5 | 2,4-Br₂—C₆H₃—O—C₆H₃(NO₂)—OCH₂—[spiro dioxolane] | $n_D^{26.5}$ 1.5932 |

TABLE 1-continued

| Compd. No. | Chemical Structure | Physical Properties |
|---|---|---|
| 6 | 2-Cl-4-CF$_3$-phenyl-O-(4-NO$_2$-3-(OCH$_2$-(1,4-dioxaspiro[4.4]nonan-2-yl))phenyl) ether | $n_D^{25}$ 1.5411 |
| 7 | 2,4,6-trichlorophenyl-O-(4-NO$_2$-3-(OCH$_2$-(1,4-dioxaspiro[4.4]nonan-2-yl))phenyl) ether | $n_D^{25.1}$ 1.5481 |
| 8 | 2,4-dichlorophenyl-O-(4-NO$_2$-3-(OCH$_2$-(2,2-bis(chloromethyl)-1,3-dioxolan-4-yl))phenyl) ether | $n_D^{25}$ 1.5954 |
| 9 | 2-Cl-4-CF$_3$-phenyl-O-(4-NO$_2$-3-(OCH$_2$-(2,2-bis(chloromethyl)-1,3-dioxolan-4-yl))phenyl) ether | $n_D^{25}$ 1.5453 |
| 10 | 2,4,6-trichlorophenyl-O-(4-NO$_2$-3-(OCH$_2$-(2,2-bis(chloromethyl)-1,3-dioxolan-4-yl))phenyl) ether | $n_D^{29}$ 1.5920 |
| 11 | 2-Cl-4-CF$_3$-phenyl-O-(4-NO$_2$-3-(OCH$_2$-(2-methyl-2-chloromethyl-1,3-dioxolan-4-yl))phenyl) ether | $n_D^{25}$ 1.5369 |

TABLE 1-continued

| Compd. No. | Chemical Structure | Physical Properties |
|---|---|---|
| 12 | 2,4,6-trichlorophenyl ether of 4-nitro-3-[(2-chloromethyl-2-methyl-1,3-dioxolan-4-yl)methoxy]phenyl; Ar = 2,4,6-Cl$_3$-C$_6$H$_2$-O-C$_6$H$_3$(NO$_2$)-OCH$_2$-[dioxolane with CH$_3$ and CH$_2$Cl] | m.p. 117.5–126.5° C. |
| 13 | 2,4-Cl$_2$-C$_6$H$_3$-O-C$_6$H$_3$(NO$_2$)-OCH$_2$-[dioxolane with C$_2$H$_5$ and C$_2$H$_5$] | $n_D^{26.6}$ 1.5720 |
| 14 | 2-Cl-4-CF$_3$-C$_6$H$_3$-O-C$_6$H$_3$(NO$_2$)-OCH$_2$-[dioxolane with C$_2$H$_5$ and C$_2$H$_5$] | $n_D^{25}$ 1.5326 |
| 15 | 2,4-Cl$_2$-C$_6$H$_3$-O-C$_6$H$_3$(NO$_2$)-OCH$_2$-[dioxolane with CH$_3$ and C$_2$H$_5$] | m.p. 70.5–73° C. |
| 16 | 2-Cl-4-CF$_3$-C$_6$H$_3$-O-C$_6$H$_3$(NO$_2$)-OCH$_2$-[dioxolane with CH$_3$ and C$_2$H$_5$] | $n_D^{25}$ 1.5328 |
| 17 | 4-Cl-C$_6$H$_4$-O-C$_6$H$_3$(NO$_2$)-OCH$_2$-[dioxolane with CH$_3$ and CH$_3$] | $n_D^{25.5}$ 1.5768 |

TABLE 1-continued

| Compd. No. | Chemical Structure | Physical Properties |
|---|---|---|
| 18 | 4-Br-C6H4-O-[3-(OCH2-C(CH3)2-O-O)-4-NO2-C6H3] | m.p. 84–88° C. |
| 19 | 2,4-Cl2-C6H3-O-[3-(OCH2-C(CH3)2-O-O)-4-NO2-C6H3] | $n_D^{23.3}$ 1.5640 |
| 20 | 4-Br-2-Cl-C6H3-O-[3-(OCH2-C(CH3)2-O-O)-4-NO2-C6H3] | $n_D^{25}$ 1.5932 |
| 21 | 4-Cl-2-Br-C6H3-O-[3-(OCH2-C(CH3)2-O-O)-4-NO2-C6H3] | $n_D^{25}$ 1.5738 |
| 22 | 2,4-Br2-C6H3-O-[3-(OCH2-C(CH3)2-O-O)-4-NO2-C6H3] | $n_D^{25}$ 1.5791 |
| 23 | 4-Cl-2-F-C6H3-O-[3-(OCH2-C(CH3)2-O-O)-4-NO2-C6H3] | $n_D^{25.5}$ 1.5620 |

TABLE 1-continued
| Compd. No. | Chemical Structure | Physical Properties |
|---|---|---|
| 24 | 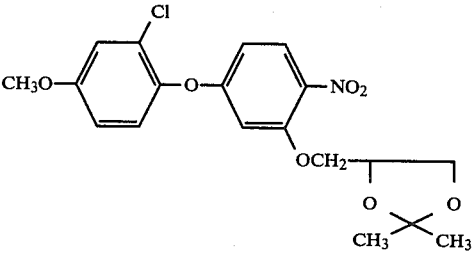 | $n_D^{25.5}$ 1.5692 |
| 25 | 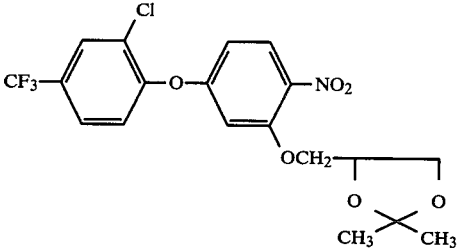 | $n_D^{24.5}$ 1.5412 |
| 26 | 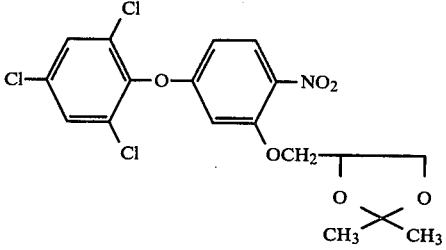 | m.p. 116–118° C. |
| 27 | 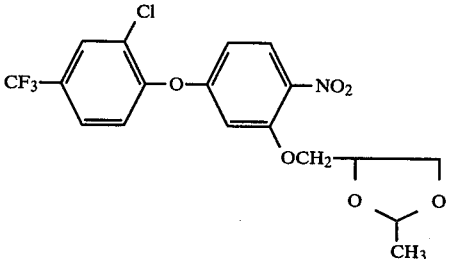 | $n_D^{25}$ 1.5432 |
| 28 | 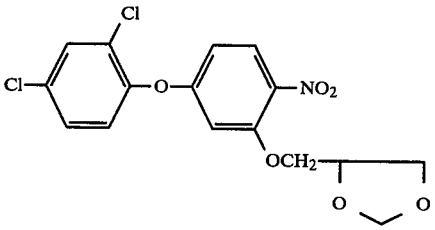 | $n_D^{26.6}$ 1.6009 |
| 29 | 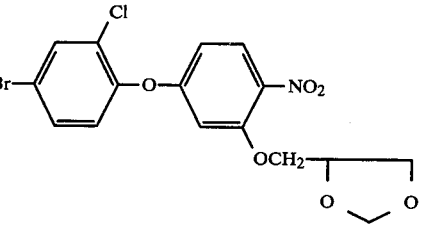 | $n_D^{28}$ 1.6150 |

TABLE 1-continued

| Compd. No. | Chemical Structure | Physical Properties |
|---|---|---|
| 30 | 4-Cl-2-Br-phenyl ether of 4-nitro-3-(1,3-dioxolan-2-ylmethoxy)phenyl | $n_D^{27}$ 1.6037 |
| 31 | 2,4-diBr-phenyl ether of 4-nitro-3-(1,3-dioxolan-2-ylmethoxy)phenyl | $n_D^{27}$ 1.6040 |
| 32 | 2,4,6-triCl-phenyl ether of 4-nitro-3-(1,3-dioxolan-2-ylmethoxy)phenyl | m.p. 105–108° C. |
| 33 | 4-CF$_3$-2-Cl-phenyl ether of 4-nitro-3-(1,3-dioxolan-2-ylmethoxy)phenyl | $n_D^{26.2}$ 1.5581 |
| 34 | 2,4-diBr-phenyl ether of 4-nitro-3-((5-chloromethyl-5-methyl-1,3-dioxan-2-yl)methoxy)phenyl | $n_D^{25}$ 1.5959 |
| 35 | 4-Cl-2-Br-phenyl ether of 4-nitro-3-((5-chloromethyl-5-methyl-1,3-dioxan-2-yl)methoxy)phenyl | $n_D^{25}$ 1.5720 |

TABLE 1-continued

| Compd. No. | Chemical Structure | Physical Properties |
|---|---|---|
| 36 | 4-Br-C6H4-O-(3-OCH2-C(CH3)(CH2Cl)(O-O ketal)-4-NO2-C6H3) | $n_D^{25}$ 1.5741 |
| 37 | 2-Cl-4-Br-C6H3-O-(3-OCH2-C(CH3)(CH2Cl)(O-O ketal)-4-NO2-C6H3) | $n_D^{25}$ 1.5691 |
| 38 | 2,4-Cl2-C6H3-O-C6H3(NO2)-O-CH(CH2-O-CH2-O) | m.p. 134–136° C. |
| 39 | 2,4,6-Cl3-C6H2-O-(4-NO2-C6H3)-O-CH(CH2-O-CH2-O) | m.p. 154–156° C. |
| 40 | 2-Cl-4-CF3-C6H3-O-(4-NO2-C6H3)-O-CH(CH2-O-CH2-O) | m.p. 105.5–108° C. |
| 41 | 2,4-Cl2-C6H3-O-(4-NO2-C6H3)-O-CH(CH2-O-CH(CH3)-O) | m.p. 120.5–122° C. |
| 42 | 2,4,6-Cl3-C6H2-O-(4-NO2-C6H3)-O-CH(CH2-O-CH(CH3)-O) | m.p. 131–134° C. |

TABLE 1-continued

| Compd. No. | Chemical Structure | Physical Properties |
|---|---|---|
| 43 | CF₃-C₆H₃(Cl)-O-C₆H₃(NO₂)-O-CH₂-CH(-O-)(-O-)CH-CH₃ (1,3-dioxolane with CH₃) | m.p. 108–110° C. |
| 44 | Cl,Cl,F-C₆H₂-O-C₆H₃(NO₂)-OCH₂-C(CH₃)(CH₃) cyclic acetal | $n_D^{23.5}$ 1.5658 |
| 45 | Cl,Cl,F-C₆H₂-O-C₆H₃(NO₂)-O-CH(CH₂O-)(CH₂O-)CH (1,3-dioxane) | $n_D^{24}$ 1.5801 |
| 46 | Cl-C₆H₄-O-C₆H₃(NO₂)-OSO₂CH₃ | m.p. 100–103° C. |
| 47 | Cl-C₆H₄-O-C₆H₃(NO₂)-OSO₂CH₂CH₃ | m.p. 48–50° C. |
| 48 | Br-C₆H₄-O-C₆H₃(NO₂)-OSO₂CH₃ | m.p. 109–111° C. |
| 49 | Br-C₆H₄-O-C₆H₃(NO₂)-OSO₂CH₂CH₃ | $n_D^{22}$ 1.5913 |
| 50 | Br-C₆H₄-O-C₆H₃(NO₂)-OSO₂CH₂CH₂CH₃ | $n_D^{22}$ 1.5808 |

TABLE 1-continued

| Compd. No. | Chemical Structure | Physical Properties |
|---|---|---|
| 51 | Br—C$_6$H$_4$—O—C$_6$H$_3$(NO$_2$)(OSO$_2$CH$_2$CH$_2$CH$_2$CH$_3$) | $n_D^{22}$ 1.5811 |
| 52 | Br—C$_6$H$_4$—O—C$_6$H$_3$(NO$_2$)(OSO$_2$N(CH$_3$)$_2$) | $n_D^{23}$ 1.6553 |
| 53 | 2,4-Cl$_2$C$_6$H$_3$—O—C$_6$H$_3$(NO$_2$)(OSO$_2$CH$_3$) | m.p. 97–99° C. |
| 54 | 2,4-Cl$_2$C$_6$H$_3$—O—C$_6$H$_3$(NO$_2$)(OSO$_2$CH$_2$CH$_3$) | m.p. 88–90° C. |
| 55 | 2,4-Cl$_2$C$_6$H$_3$—O—C$_6$H$_3$(NO$_2$)(OSO$_2$CH$_2$CH$_2$CH$_3$) | m.p. 73–76° C. |
| 56 | 2,4-Cl$_2$C$_6$H$_3$—O—C$_6$H$_3$(NO$_2$)(OSO$_2$CH(CH$_3$)$_2$) | m.p. 122–125° C. |
| 57 | 2,4-Cl$_2$C$_6$H$_3$—O—C$_6$H$_3$(NO$_2$)(OSO$_2$CH$_2$CH$_2$CH$_2$CH$_3$) | m.p. 55.5–58° C. |
| 58 | 2,4-Cl$_2$C$_6$H$_3$—O—C$_6$H$_3$(NO$_2$)(OSO$_2$CH$_2$Cl) | m.p. 76–78° C. |

TABLE 1-continued
| Compd. No. | Chemical Structure | Physical Properties |
|---|---|---|
| 59 | 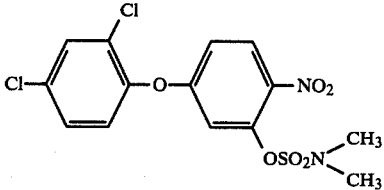 | m.p. 91–93° C. |
| 60 | 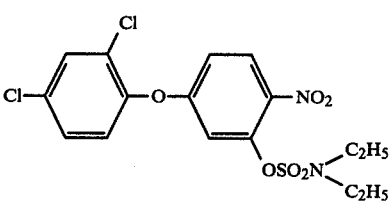 | m.p. 69–71.5° C. |
| 61 | 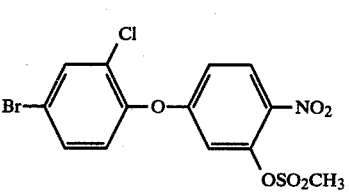 | m.p. 83–87° C. |
| 62 | 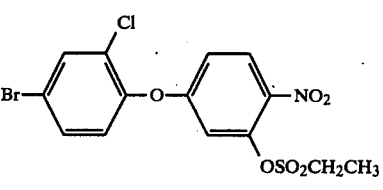 | $n_D^{22}$ 1.5968 |
| 63 | 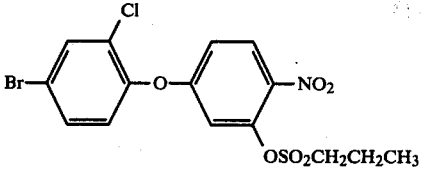 | $n_D^{22}$ 1.5842 |
| 64 | 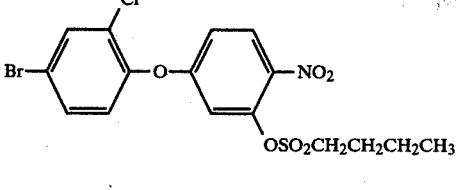 | $n_D^{22}$ 1.5811 |
| 65 | 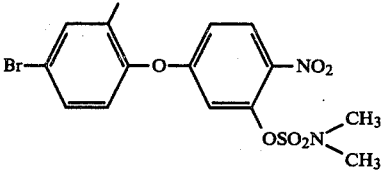 | $n_D^{23}$ 1.6598 |
| 66 | 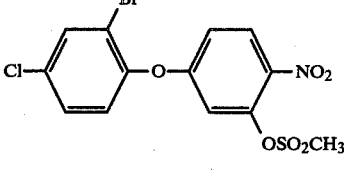 | m.p. 95–98° C. |

TABLE 1-continued
| Compd. No. | Chemical Structure | Physical Properties |
|---|---|---|
| 67 | 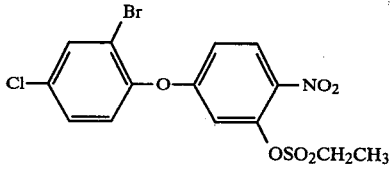 | $n_D^{22}$ 1.5944 |
| 68 | 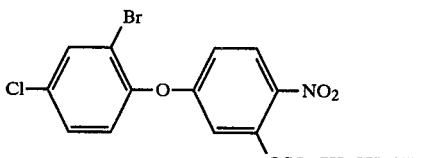 | $n_D^{22}$ 1.5886 |
| 69 | 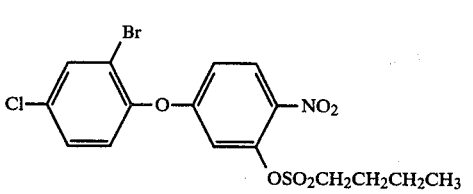 | $n_D^{22}$ 1.5692 |
| 70 | 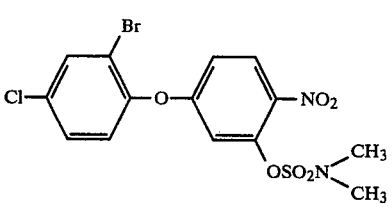 | $n_D^{24}$ 1.6301 |
| 71 | 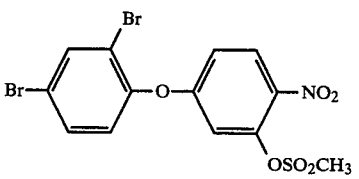 | m.p. 122–124° C. |
| 72 | 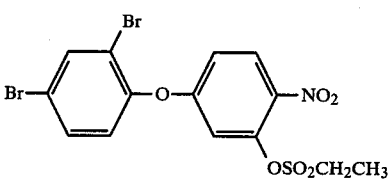 | m.p. 85–87° C. |
| 73 | 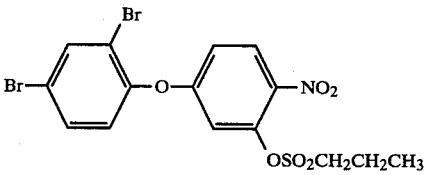 | $n_D^{22}$ 1.5986 |
| 74 | 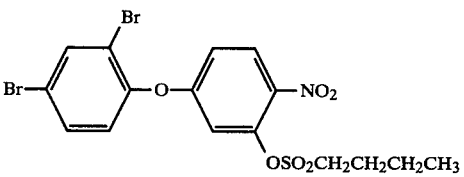 | $n_D^{22}$ 1.5931 |

TABLE 1-continued
| Compd. No. | Chemical Structure | Physical Properties |
|---|---|---|
| 75 | 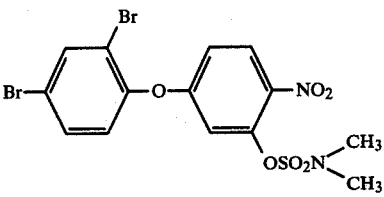 | m.p. 109–111° C. |
| 76 | 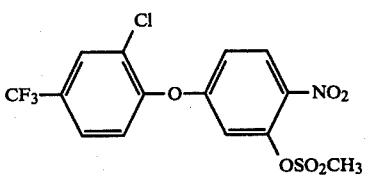 | m.p. 64–65° C. |
| 77 | 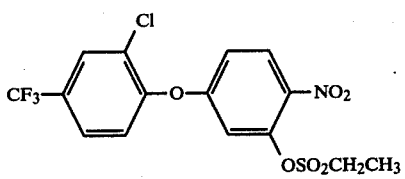 | m.p. 60–62° C. |
| 78 | 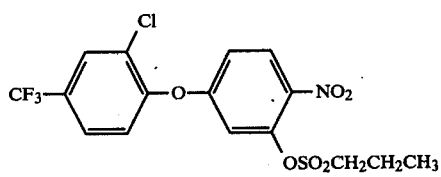 | $n_D^{21.5}$ 1.5439 |
| 79 | 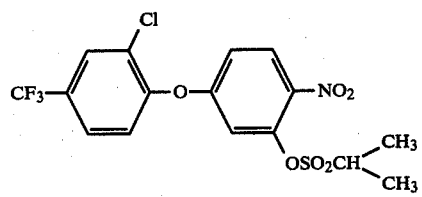 | $n_D^{27.5}$ 1.5428 |
| 80 | 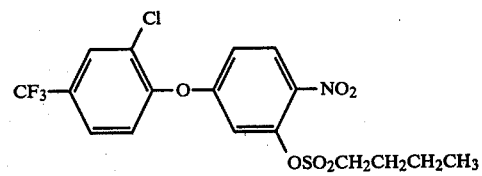 | $n_D^{21.5}$ 1.5351 |
| 81 | 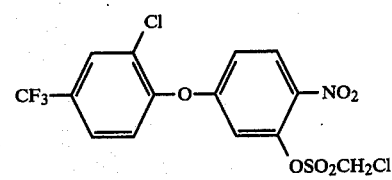 | $n_D^{15}$ 1.5633 |
| 82 | 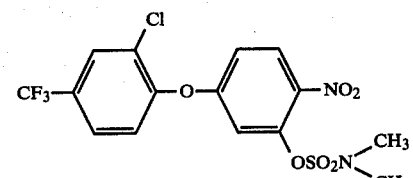 | m.p. 89–91° C. |

TABLE 1-continued

| Compd. No. | Chemical Structure | Physical Properties |
|---|---|---|
| 83 | CF$_3$-C$_6$H$_3$(Cl)-O-C$_6$H$_3$(NO$_2$)-OSO$_2$N(C$_2$H$_5$)$_2$ | $n_D^{27.5}$ 1.5345 |
| 84 | 2,4,6-Cl$_3$C$_6$H$_2$-O-C$_6$H$_3$(NO$_2$)-OSO$_2$CH$_3$ | m.p. 168–171° C. |
| 85 | 2,4,6-Cl$_3$C$_6$H$_2$-O-C$_6$H$_3$(NO$_2$)-OSO$_2$CH$_2$CH$_3$ | m.p. 116–120° C. |
| 86 | 2,4,6-Cl$_3$C$_6$H$_2$-O-C$_6$H$_3$(NO$_2$)-OSO$_2$CH$_2$CH$_2$CH$_3$ | m.p. 99–101° C. |
| 87 | 2,4,6-Cl$_3$C$_6$H$_2$-O-C$_6$H$_3$(NO$_2$)-OSO$_2$CH$_2$CH$_2$CH$_2$CH$_3$ | m.p. 97–99° C. |
| 88 | 2,4,6-Cl$_3$C$_6$H$_2$-O-C$_6$H$_3$(NO$_2$)-OSO$_2$CH$_2$Cl | m.p. 95–97° C. |
| 89 | 2,4,6-Cl$_3$C$_6$H$_2$-O-C$_6$H$_3$(NO$_2$)-OSO$_2$N(CH$_3$)$_2$ | m.p. 89–92° C. |
| 90 | 2,4,6-Cl$_3$C$_6$H$_2$-O-C$_6$H$_3$(NO$_2$)-OSO$_2$N(C$_2$H$_5$)$_2$ | m.p. 104.5–107° C. |

TABLE 1-continued

| Compd. No. | Chemical Structure | Physical Properties |
|---|---|---|
| 91 | ![structure] | m.p. 109–111° C. |

Among the compounds as enumerated above, the following compounds are preferred in view of the higher herbicidal activity:

2-Chloro-4-trifluoromethyl-3'-{(1,3-dioxorane-2,2-dimethyl-4-yl)methoxy}-4'-nitrodiphenyl ether (Compound No. 25);

2,4,6-Trichloro-3'-{(1,3-dioxorane-2,2-dimethyl-4-yl)methoxy}-4'-nitrodiphenyl ether (Compound No. 26);

2-Chloro-4-trifluoromethyl-3'-{(1,3-dioxorane-2-methyl-4-yl)methoxy}-4'-nitrodiphenyl ether (Compound No. 27);

2,4,6-Trichloro-3'-{(1,3-dioxorane-4-yl)methoxy}-4'-nitrodiphenyl ether (Compound No. 32);

2-Chloro-4-trifluoromethyl-3'-{(1,3-dioxorane-4-yl)methoxy}-4'-nitrodiphenyl ether (Compound No. 33);

2-Chloro-4-trifluoromethyl-3'-(1,3-dioxa-5-cyclohexyloxy)-4'-nitrodiphenyl ether (Compound No. 40);

2-Chloro-4-trifluoromethyl-3'-(1,3-dioxa-2-methyl-5-cyclohexyloxy)-4'-nitrodiphenyl ether (Compound No. 43);

2,4-Dichloro-6-fluoro-3'-(1,3-dioxa-5-cyclohexyloxy)-4'-nitrodiphenyl ether (Compound No. 45);

2-Chloro-4-trifluoromethyl-3'-isopropane-sulfonyloxy-4'-nitrodiphenyl ether (Compound No. 79);

2-Chloro-4-trifluoromethyl-3'-chloromethane-sulfonyloxy-4'-nitrodiphenyl ether (Compound No. 81); and 2-Chloro-4-trifluoromethyl-3'-N,N-dimethyl-sulfamoyloxy-4'-nitrodiphenyl ether (Compound No. 82)

The diphenyl ether derivatives of the present invention can be synthesized according to the following reaction steps.

Step 1

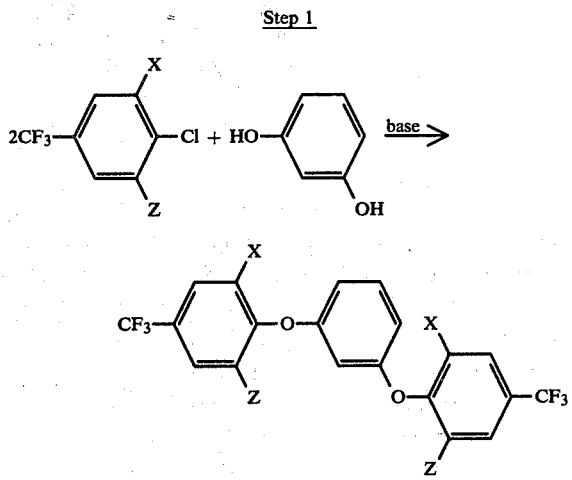

(wherein X and Z each represent a hydrogen atom or a halogen atom)

In the above reaction, there may be employed a solvent soluble in water, having a boiling point of 150° C. or higher, such as dimethyl sulfoxide, dimethylformamide, dimethylacetamide, sulforane, etc. Suitable bases to be used are potassium hydroxide, sodium hydroxide, potassium carbonate, and the like. The reaction may be carried out at a temperature preferably in the range from 150° to 250° C. for 30 to 60 hours.

Step 2

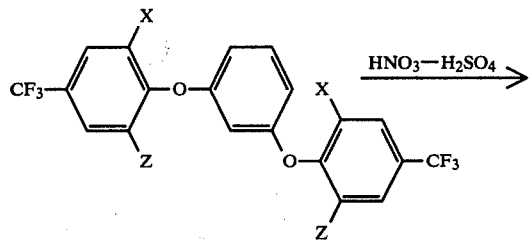

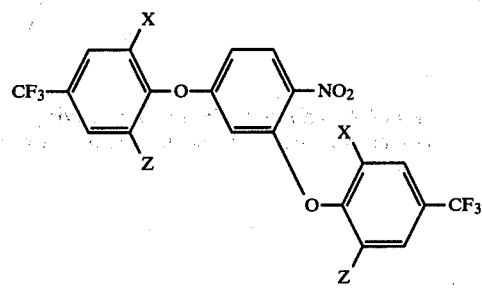

In the above reaction, there may be employed a mixed acid containing sulfuric acid and nitric acid at mixing ratios as used in conventional nitration reaction, but it is preferred to use a nitric acid with a concentration of 61 to 80% in an amount of 2.5 to 4 times as much as the moles to be reacted and to use sulfuric acid in an amount of 1.3 to 1.6 times as much as the moles of nitric acid. The reaction temperature may preferably be in the range from 10° to 30° C.

Alternatively, when it is desired to prepare a diphenyl ether derivative (I) of the present invention wherein the substituent Y is a halogen atom or methoxy, Steps 1 and 2 can be replaced by the following Step to give a corresponding intermediate derivative:

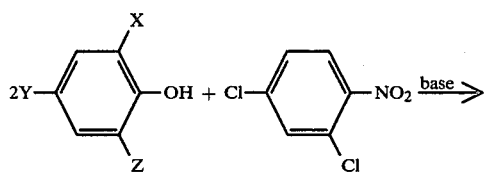

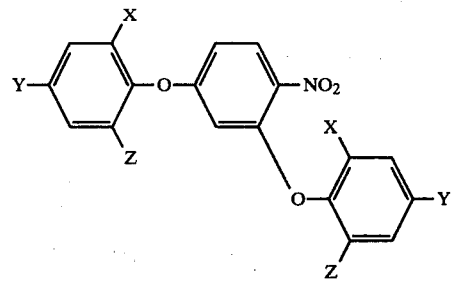

In this Step, there may be employed the same reaction conditions as in Step 1.

Step 3

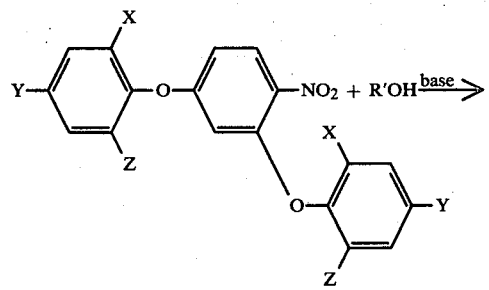

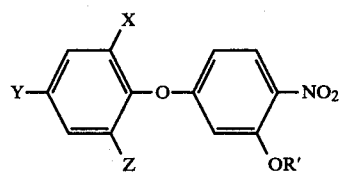

(wherein R' is a lower alkyl group, having preferably 1 to 4 carbon atoms, typically methyl, a group of the formula:

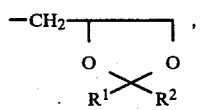

wherein each of $R^1$ and $R^2$ is a lower alkyl group, a hydrogen atom or a chloromethyl group, or $R^1$ and $R^2$ taken together may form a saturated alicyclic ring, or a group of the formula:

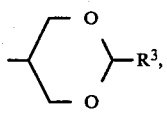

wherein $R^3$ is a hydrogen atom or a methyl group).

In Step 3, the base to be used may suitably be a strong base such as sodium hydroxide or potassium hydroxide. Such a base is to be employed preferably in an amount of 1.3 to 2.5 times as much as the moles to be reacted. The solvent may preferably be a solvent soluble in water such as dioxane, dimethylsulfoxide, dimethylformamide, dimethylacetamide or tetrahydrofuran. The reaction temperature may preferably be in the range from 20° to 80° C.

When the group R' is a group of the formula:

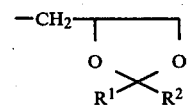

or a group of the formula:

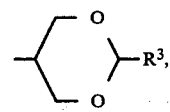

the reaction product obtained in Step 3 can be isolated from the reaction mixture to give the diphenyl ether derivative (I) of the present invention, which may further be subjected to purification by conventional procedures, if desired.

When the group R' is a lower alkyl group, the reaction product in Step 3 is further subjected to the following Steps 4 and 5.

Step 4

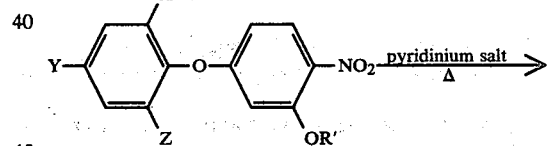

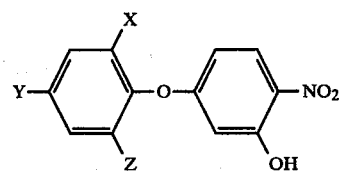

In this Step, the starting diphenyl ether derivative is fused with a salt of pyridine and a mineral acid such as hydrochloric acid, sulfuric acid and nitric acid. As the pyridinium salt, there may preferably be used pyridinium hydrochloride in an amount of 5 to 10 times as much as the moles to be reacted. The reaction may be carried out at 150° to 250° C., preferably 190° to 220° C. for 5 to 30 minutes. After completion of the reaction, the reaction mixture is cooled and poured into water. Since the unreacted starting material and the pyridinium salt are soluble in water, the desired product may be obtained by filtration of the solid substance.

Step 5

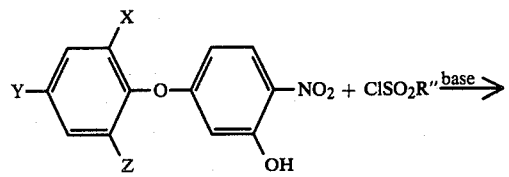

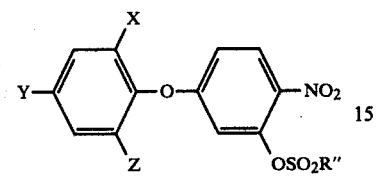

(wherein R'' is a lower alkyl group, a mono- or di-lower-alkylamino group or a mono-chloromethyl group).

The above reaction may conveniently be carried out in the presence of a solvent by adding a suitable base (e.g., pyridine, triethylamine, anhydrous sodium carbonate, anhydrous potassium carbonate, etc.). The solvent to be employed is not particularly limited, but there may be used any solvent inert to the reaction, including, for example, benzene, pyridine, acetone, dimethylformamide, dimethylacetamide, dimethylsulfoxide and a mixture thereof. The reaction temperature is not particularly limited, but the reaction may be carried out at room temperature or at a reflux temperature of the solvent employed.

In Steps 1 through 5 as described above, the reactions in Steps 1 and 2 are well known in the art, as disclosed by J. Agric. Food Chem. Vol. 23, No. 3, p. 592, 1975. Thus, the process of the present invention can be defined comprehensively as a process for producing a diphenyl ether derivative (I), which comprises reacting a compound of the formula (II):

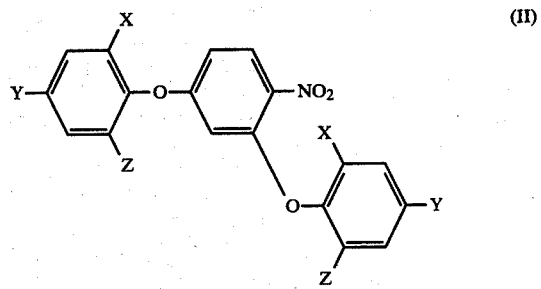

(II)

wherein X and Z each represent a hydrogen atom or a halogen atom, and Y represents a halogen atom, a trifluoromethyl group or a methoxy group,
with a compound of the formula (III):

R'—OH (III)

wherein R' represents a lower alkyl group, a group of the formula:

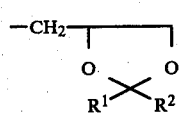

(in which each of $R^1$ and $R^2$ is a lower alkyl group, a hydrogen atom or a chloromethyl group, or $R^1$ and $R^2$ taken together may form a saturated alicyclic ring) or a group of the formula:

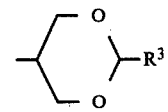

(in which $R^3$ is a hydrogen atom or a methyl group), to afford a compound of the formula (IV):

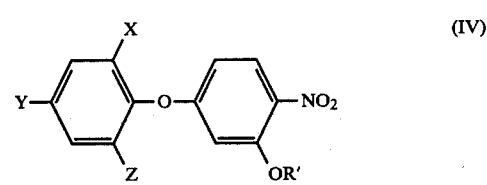

(IV)

wherein X, Y, Z, and R' have the same meanings as defined above,
and, in cases where R' is a lower alkyl group in formula (IV), further treating the compound (IV) by heating with a salt of pyridine and a mineral acid to form a compound of the formula (V):

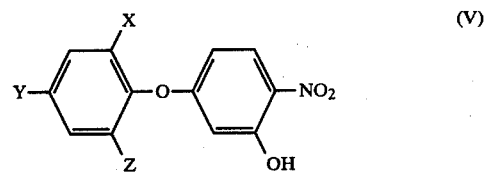

(V)

wherein X, Y and Z have the same meanings as defined above,
and then teacting the thus formed compound (V) with a compound of the formula (VI):

ClSO$_2$R'' (VI)

wherein R'' is a lower alkyl group, a mono- or di-lower-alkylamino group or a mono-chloromethyl group, to afford a compound of the formula:

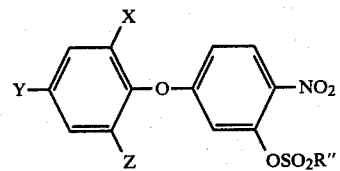

wherein X, Y, Z and R'' have the same meanings as defined above.

The above reaction steps will be more fully illustrated by the following Synthesis examples.

SYNTHESIS 1

Synthesis of 2,4-bis(2-chloro-4-trifluoromethylphenoxy)-nitrobenzene (Step 1 and Step 2)

In 100 ml of dimethyl sulfoxide, there were dissolved 129 g. (0.60 mole) of 3,4-dichlorobenzotrifluoride and 27.5 g. (0.25 mole) of resorcin. Then, a solution of 34 g.

(0.60 mole) of potassium hydroxide dissolved in 15 ml of water was added to the resultant solution and the mixture was heated with stirring at 150° to 160° C. for 50 hours. After the reaction mixture was left to cool, water was added thereto and the oily product precipitated was subjected to extraction with benzene. The extract was washed with a dilute aqueous sodium hydroxide and with water to remove unaltered resorcin, followed by drying over sodium sulfate and evaporation of benzene under reduced pressure, to give crude bis(2-chloro-4-trifluoromethylphenoxy)benzene. Subsequently, said crude bis(2-chloro-4-trifluoromethylphenoxy)benzene was added dropwise into a mixed acid comprising 60 ml of conc. nitric acid (d=1.38) and 60 ml of conc. sulfuric acid under stirring at 10° to 15° C. After completion of the dropwise addition, the mixture was further stirred at 20° to 27° C. for additional one hour to complete the reaction. Then, ice-water was added to the reaction mixture and the resultant precipitate of an oily product was extracted with benzene. The extract was washed with a dilute aqueous sodium hydroxide, and then with water, followed by drying over sodium sulfate and evaporation of benzene. Recrystallization of the residue from isopropyl alcohol gave 2,4-bis(2-chloro-4-trifluoromethylphenoxy)nitrobenzene as pale yellow powders, melting at 111° to 113° C. (yield: 47%).

SYNTHESIS 2

Synthesis of 2,4-bis(2,4-dichlorophenoxy)nitrobenzene (Step 2)

In 150 ml of dimethylacetamide, there was dissolved 114 g. (0.70 mole) of 2,4-dichlorophenol, and 28 g. (0.70 mole) of sodium hydroxide was added to the resultant solution to be dissolved therein under heating. After the solution was cooled, 57.6 g. (0.30 mole) of 2,4-dichloronitrobenzene was further added thereto and the mixture was heated with stirring at 150° to 160° C. for 9 hours. After the reaction mixture was cooled, 300 ml of water was added thereto to obtain an oily product as precipitate, which was in turn subjected to extraction with benzene. The extract was washed with a dilute aqueous sodium hydroxide, and then with water, followed by drying over sodium sulfate and evaporation of benzene under reduced pressure. The residue was subjected to recrystallization from ethanol to obtain 115 g. of 2,4-bis(2,4-dichlorophenoxy)nitrobenzene as pale yellow prisms (m.p.=91° to 93° C.; yield: 86%).

SYNTHESIS 3

Synthesis of 2,4-dichloro-3'-methoxy-4'-nitrodiphenyl ether (Step 3)

In 150 ml of dioxane was dissolved 93.5 g. (0.21 mole) of 2,4-bis(2,4-dichlorophenoxy)nitrobenzene, and to the resultant solution was added dropwise a methanolic solution containing 23.5 g. (0.42 mole) of potassium hydroxide at 25° to 30° C. After the dropwise addition was over, the mixture was further stirred at 35° to 45° C. for additional three hours to complete the reaction. Then, water was added to the reaction mixture to precipitate an oily product, which was in turn subjected to extraction with benzene. The extract was washed with a dilute aqueous sodium hydroxide, and then with water. The washed extract was dried over sodium sulfate and thereafter subjected to evaporation of the solvent under reduced pressure to give 63.0 g. of 2,4-dichloro-3'-methoxy-4'-nitrodiphenyl ether as pale yellow crystals (m.p.=112° to 114° C.; yield: 95%).

SYNTHESIS 4

Synthesis of 2-chloro-4-trifluoromethyl-3'-{(1,4-dioxaspiro[4.4]nonan-2-yl)methoxy}-4'-nitrodiphenyl ether (Compound No. 6)

In 20 ml of dioxane, there were dissolved 3.2 g. (0.006 mole) of 2,4-bis(2-chloro-4-trifluoromethylphenoxy)nitrobenzene and 1.3 g. (0.008 mole) of 1,2-cyclopentylidene glycerine. To the resultant solution was added 0.5 g. (0.008 mole) of potassium hydroxide, and the mixture was heated with stirring at about 50° C. for 8 hours. Then, the reaction mixture was cooled and water was added thereto. After the oily product precipitated was extracted with benzene, the extract was washed with water, dried over sodium sulfate and thereafter subjected to evaporation of benzene.

The residue was passed through a silica gel column to obtain 2.1 g. of 2-chloro-4-trifluoromethyl-3'-{(1,4-dioxaspiro[4.4]nonan-2-yl)methoxy}-4'-nitrodiphenyl ether as pale yellow oily product ($n_D^{25}$: 1.5411; yield: 70%).

SYNTHESIS 5

Synthesis of 2,4,6-trichloro-3'-{(1,3-dioxorane-4-yl)methoxy}-4'-nitrodiphenyl ether (Compound No. 32)

After 2.5 g. (0.005 mole) of 2,4-bis(2,4,6-trichlorophenoxy)-nitrobenzene and 0.7 g. (0.007 mole) of 1,2-methylidene glycerine were dissolved in 10 ml of dioxane, 0.5 g. (0.008 mole) of potassium hydroxide was added to the resultant solution. The mixture was heated with stirring at about 50° C. for 3 hours. The reaction mixture was then cooled, followed by addition of water, and the precipitated oily product was extracted with benzene. The extract was washed with water, dried over sodium sulfate and then subjected to evaporation of benzene.

Recrystallization of the residue from ethanol gave 0.9 g. of 2,4,6-trichloro-3'-{(1,3-dioxorane-4-yl)methoxy}-4'-nitrodiphenyl ether as colorless crystals (m.p.=105° to 108° C.; yield: 45%).

SYNTHESIS 6

Synthesis of 2-chloro-4-trifluoromethyl-3'-(1,3-dioxa-5-cyclohexyloxy)-4'-nitrodiphenyl ether (Compound No. 40)

To a solution prepared by dissolving 2.5 g. (0.005 mole) of 2,4-bis(2-chloro-4-trifluoromethylphenoxy)nitrobenzene and 0.7 g. (0.007 mole) of 1,3-methylidene glycerine in 10 ml of dioxane, there was added 0.5 g. (0.008 mole) of potassium hydroxide, and the mixture was heated with stirring at about 50° C. for 8 hours. After the reaction mixture was cooled, water was added thereto to precipitate an oily product. Said oily product was subjected to extraction with benzene and the extract was washed with water, followed by drying over sodium sulfate and evaporation of benzene.

Recrystallization of the residue from ethanol gave 1.2 g. of 2-chloro-4-trifluoromethyl-3'-(1,3-dioxa-5-cyclohexyloxy)-4'-nitrodiphenyl ether as colorless crystals (m.p.=105.5° to 108° C.; yield: 60%).

SYNTHESIS 7

Synthesis of 2-chloro-4-trifluoromethyl-3'-{(1,3-dioxorane-4-yl)methoxy}-4'-nitrodiphenyl ether (Compound No. 33)

To a solution prepared by dissolving 2.5 g. (0.005 mole) of 2,4-bis(2-chloro-4-trifluoromethylphenoxy)nitrobezene and 0.7 g. (0.007 mole) of 1,2-methylidene glycerine in 20 ml of dioxane, there was added 0.5 g. (0.008 mole) of potassium hydroxide, and the mixture was heated with stirring at about 50° C. for 8 hours. After treatment of the reaction mixture conducted similarly as described in Synthesis 6, the residue obtained was subjected to silica gel column chromatography using a benzene-n-hexane mixture as eluant. As the result, there was obtained 1.3 g. of 2-chloro-4-trifluoromethyl-3'-{(1,3-dioxorane-4-yl)methoxy}-4'-nitrodiphenyl ether as pale yellow oily liquid ($n_D^{26.2}$: 1.5581; yield: 65%).

SYNTHESIS 8

Synthesis of 2-chloro-4-trifluoromethyl-3'-{(1,3-dioxorane-2,2-dimethyl-4-yl)methoxy}-4'-nitrodiphenyl ether (Compound No. 25)

To a solution prepared by dissolving 1.8 g. (0.004 mole) of 2,4-bis(2-chloro-4-trifluoromethylphenoxy)nitrobenzene and 0.8 g. (0.006 mole) of 1,2-iso-propylidene glycerine in 10 ml of dioxane, there was added 0.4 g. (0.007 mole) of potassium hydroxide. The reaction and the treatment of the reaction product were conducted in the same manner as in Synthesis 7, followed by silica gel chromatography of the residue using a benzene-n-hexane mixture as eluant, to give 0.7 g. of 2-chloro-4-trifluoromethyl-3'-{(1,3-dioxorane-2,2-dimethyl-4-yl)methoxy}-4'-nitrodiphenyl ether as pale yellow oily liquid ($n_D^{24.5}$: 1.5412; yield: 41%).

SYNTHESIS 9

Synthesis of 2,4-dichloro-3'-hydroxy-4'-nitrodiphenyl ether (Step 4)

A well-mixed mixture comprising 6.2 g (0.020 mole) of the compound 2,4-dichloro-3'-methoxy-4'-nitrophenyl ether and 23.1 g. (0.199 mole) of pyridinium hydrochloride was heated with stirring at 190° to 205° C. for 20 minutes. After cooling, 100 ml of water was added to the reaction mixture. The resultant precipitate was subjected to extraction with benzene and the extract was washed with a saturated aqueous sodium chloride, followed by drying over sodium sulfate and evaporation of the solvent. The residue was subjected to recrystallization from ethanol to obtain 5.3 g. of 2,4-dichloro-3'-hydroxy-4'-nitrodiphenyl ether as yellow prisms (m.p.=75° to 77° C.; yield: 88%).

SYNTHESIS 10

Synthesis of 2,4-dichloro-3'-methanesulfonyloxy-4'-nitrodiphenyl ether (Compound No. 53)

While stirring a solution having 3.0 g. (0.01 mole) of 2,4-dichloro-3'-hydroxy-4-nitrodiphenyl ether dissolved in 20 ml of pyridine under-ice-cooling, there was added dropwise thereto 2.3 g. (0.02 mole) of methanesulfonyl chloride. After the dropwise addition, the mixture was continued to be stirred at room temperature overnight. Then, water was added to the reaction mixture to obtain an oily product as precipitate, which was in turn subjected to extraction with benzene. The extract was washed with a dilute aqueous sodium hydroxide and with water, followed by drying over sodium sulfate and evaporation of benzene. By recrystallization of the residue from ethanol, there was obtained 3.7 g. of 2,4-dichloro-3'-methanesulfonyloxy-4'-nitrodiphenyl ether as pale yellow prisms (m.p.=97° to 99° C.; yield: 98%).

SYNTHESIS 11

Synthesis of 2-chloro-4-trifluoromethyl-3'-N,N-dimethylsulfamoyloxy-4'-nitrodiphenyl ether (Compound No. 82)

After 3.3 g. (0.01 mole) of 2-chloro-4-trifluoromethyl-3'-hydroxy-4'-nitrodiphenyl ether and 1.6 g. (0.013 mole) of dimethylaminosulfamoyl chloride were dissolved in 25 ml of dimethylacetamide, 2.8 g. (0.02 mole) of anhydrous potassium carbonate was added to the resultant solution. The mixture was subjected to heating with stirring at about 150° C. for 5 hours. Then, the reaction mixture was left to cool and water was added to the mixture to obtain an oily product as precipitate. Said oily product was subjected to extraction with benzene and the extract was washed with a dilute aqueous sodium hydroxide, and then with water, followed by drying over sodium sulfate and evaporation of benzene. Recrystallization of the residue from ethanol gave 3.0 g. of 2-chloro-4-trifluoromethyl-3'-N,N-dimethylsulfamoyloxy-4'-nitrodiphenyl ether as pale yellow needles (m.p.=89° to 91° C.; yield: 68%).

SYNTHESIS 12

Synthesis of 2-chloro-4-trifluoromethyl-3'-chloromethanesulfonyloxy-4'-nitrodiphenyl ether (Compound No. 81)

To a solution prepared by dissolving 3.3 g. (0.0099 mole) of 2-chloro-4-trifluoromethyl-3'-hydroxy-4'-nitrodiphenyl ether, which had been synthesized according to the same method as in Synthesis 9, in 30 ml of benzene 5 ml of pyridine, there was added dropwise a solution of 2.3 g. (0.015 mole) of chloromethanesulfonyl chloride in 5 ml of benzene. After the dropwise addition was over, the mixture was continued to be stirred at room temperature overnight. The oily product precipitated by addition of water to the reaction mixture was extracted with benzene. The extract was washed with a dilute hydrochloride acid, with a dilute aqueous sodium hydroxide and then with water. After drying over sodium sulfate, followed by evaporation of benzene under reduced pressure, the resultant residue was subjected to silica gel column chromatography using a benzene-n-hexane mixture as eluant to give 2.5 g. of 2-chloro-4-trifluoromethyl-3'-chloromethanesulfonyloxy-4'-nitrodiphenyl ether as pale red oily liquid ($n_D^{15.0}$: 1.5633; yield: 56%).

In another aspect of this invention, there is provided a herbicidal composition which comprises as an active ingredient the diphenyl ether derivative of the above formula (I) and an agriculturally acceptable carrier.

When the diphenyl ether derivative of this invention is to be applied as herbicides, the derivative may be formulated for use to the preparations commonly employed as a herbicide, for example, dusts, granules, wettable powders, emulsifiable concentrates, water soluble powders, liquid formulations and so on, with admixture of an inert carrier and, if required, other auxiliary agents.

As the inert carrier, there may be mentioned any of solid, liquid or gaseous carriers ordinarily employed in the art for herbicides and, for example, talc, clay, kaolin, diatomaceous earth, calcium carbonate, bentonite, white carbon, benzene, xylene, n-hexane, methylnaphthalene, cyclohexanone, isophoron and the like.

The herbicidal composition of this invention may also optionally be blended with any auxiliary agents for preparation, for example, spreaders, diluents, surface active agents, solvents and the like as usually done in the art.

Moreover, the herbicidal composition of this invention may also be admixed with other herbicides, fungicides, insecticides, other agricultural chemicals, fertilizers, e.g. urea, ammonium sulfate, ammonium phosphate, potassic fertilizers, soil conditioners and the like.

As the herbicides which may advantageously be admixed with the compound of formula (I), there may be mentioned a thiocarbamate type herbicide such as Benthiocarb (Saturn), Molinate (Ordram), etc,; an acid amide type herbicide such as Alachlor (Rasso), Butachlor (Machete), etc,; a phenoxy type herbicide such as 2,4-PA, MCP, etc.; a diphenyl ether type herbicide such as Nitrofen (NIP), Chlornitrofen (MO), etc.; a urea type herbicide such as Diuron (Karmex D), Linuron (Afalon), etc.; a triazine type herbicide such as Simazin (Prinsep). Afrazin (Gesaprim), etc.; and other herbicides such as Trifluorolin (Treflan), Oxadiazon (Ronstar), ACN (Mogeton), Bentaron (Basagran), etc.

The above-mentioned carriers and various auxiliary agents may be optionally utilized alone or in combination therewith for desired purposes.

In general, the herbicidal composition of this invention may contain the diphenyl ether derivative in an amount of 0.1-99% by weight, based upon the finished composition and the content of the active derivative in a herbicidal composition may usually depend upon the preparation form to be formulated, for instance, ordinarily 1-25 parts by weight for dusts, 25-90 parts by weight for wettable powders, 1-35 parts by weight for granules, 5-50 parts by weight for emulsifiable concentrates and the like.

The amount of the herbicidal composition to be applied usually to a field is 1-100 g/a with respect to the active ingredient of this invention.

Examples of the preparation of the present herbicidal composition are given below. All parts are given by weight hereinafter unless otherwise stated.

EXAMPLE 1

Granules 8 parts of 2-chloro-4-trifluoromethyl-3'-{(1,4-dioxaspiro-[4.4]nonan-2-yl)methoxy}-4'-nitrodiphenyl ether (Compound No. 6), 30 parts of bentonite, 59 parts of talc, 1 part of "Neopelex powder" (trade name of surfactant from Kao-Atlas K.K.) and 2 parts of sodium lignosulfonate were homogeneously blended. To the blend was added a small amount of water and the mixture was kneaded, granulated and dried to give granules.

EXAMPLE 2

Wettable powders 50 parts of 2-chloro-4-trifluoromethyl-3'-{(2,2-dimethyl-1,3-dioxorane-4-yl)methoxy}-4'-nitrodiphenyl ether (Compound No. 25), 48 parts of Kaolin and 2 parts of Neopelex powder was homogeneously blended and pulverized to give wettable powders.

EXAMPLE 3

Emulsifiable concentrates 50 parts of 2,4,6-trichloro-3'-{(1,3-dioxorane-4-yl)methoxy}-4'-nitrodiphenyl ether (Compound No. 32), 40 parts of xylene, 5 parts of dimethylformamide and 5 parts of "Toxanon" (trade name of surfactant from Sanyo Kasei Kogyo K.K.) were homogeneously blended and dissolved to give emulsifiable concentrates.

EXAMPLE 4

Dusts 5 parts of 2-chloro-4-trifluoromethyl-3'-(1,3-dioxa-5-cyclohexyloxy)-4'-nitrodiphenyl ether (Compound No. 40), 50 parts of talc and 45 parts of Kaolin were homogeneously blended to give dusts.

Experimental examples of the present herbicidal compositions are given below in order to illustrate herbicidal effects of the present composition more fully. In these Experiments, the test compounds' numbers are the same Compound Nos. as designated hereinabove and the test compounds are applied in the form of the wettable powder prepared according to the procedures of the above Example 2, which is used after dilution with water to a concentration of the active ingredient of 1000 ppm.

EXPERIMENT 1

Water surface application (soil treatment) tests for paddy field weed control (A) Wagner pots, each having the surface of 1/5000 are, were packed with Ube soil (alluvial soil) and planted with dormancy-broken seeds of barnyardgrass, tubers of flatstage (*Cyperus serotinus* Rottb.) and of arrowhead (*Sagittaria pygmaea* Miq.) and stocks of slender spikerush (*Eleocharis acienlaris* Roem.). Then, the pots were slightly covered with soil and seeds of monochoria (*Monochoria vaginalis* Presl.), of "Hotarui" (*Scirpus hotarui* Ohwi), of smallflower umbrellaplant (*Cyperus difformis* L.) and of toothcup (*Rotala indica*. Koekne) were sowed thereover and rice plant seedlings at 2 to 3 leaf stage (variety: Nihonbare) were also transplanted. Then the pots were filled with water to a depth of 3 cm.

Each test compound in the indicated dose was applied dropwise with a pipette and the pots were kept in a glass chamber at an average temperature of approximately 25° C.

After 3 weeks from the treatment, herbicidal effects of each test compound were investigated.

The results are summarized in the following Table 2 wherein herbicidal effects were evaluated according to the rating system as defined below:
5=All killed; 4=Severely damaged;
3=Moderately damaged; 2=Slightly damaged;
1=Minor damaged; 0=None (normal development)

TABLE 2

| Test compound No. | Dose g/a | Rice seedlings | Barnyard-grass | Slender spike-rush | Flat stage | Scirpus hotarui | Cyperus difformis | Monochoria | Toothcup | Arrowhead |
|---|---|---|---|---|---|---|---|---|---|---|
| 1 | 20 | 0 | 3 | 2 | 2 | 3 | 5 | 5 | 5 | 3 |
|   | 10 | 0 | 1 | 1 | 1 | 2 | 5 | 5 | 5 | 2 |
|   | 5 | 0 | 0 | 0 | 0 | 0 | 5 | 5 | 5 | 0 |
| 2 | 20 | 0 | 5 | 4 | 3 | 5 | 5 | 5 | 5 | 4 |
|   | 10 | 0 | 3 | 2 | 2 | 4 | 5 | 5 | 5 | 3 |
|   | 5 | 0 | 2 | 2 | 1 | 3 | 5 | 5 | 5 | 2 |
| 3 | 20 | 0 | 4 | 3 | 3 | 5 | 5 | 5 | 5 | 4 |
|   | 10 | 0 | 3 | 2 | 2 | 4 | 5 | 5 | 5 | 3 |
|   | 5 | 0 | 1 | 1 | 1 | 3 | 5 | 5 | 5 | 1 |
| 4 | 20 | 0 | 4 | 3 | 3 | 5 | 5 | 5 | 5 | 4 |
|   | 10 | 0 | 3 | 2 | 1 | 3 | 5 | 5 | 5 | 2 |
|   | 5 | 0 | 2 | 1 | 0 | 2 | 5 | 5 | 5 | 0 |
| 5 | 20 | 0 | 3 | 2 | 2 | 5 | 5 | 5 | 5 | 3 |
|   | 10 | 0 | 3 | 2 | 2 | 3 | 5 | 5 | 5 | 3 |
|   | 5 | 0 | 1 | 1 | 0 | 2 | 5 | 5 | 5 | 1 |
| 6 | 20 | 0 | 5 | 5 | 5 | 5 | 5 | 5 | 5 | 5 |
|   | 10 | 0 | 5 | 5 | 5 | 5 | 5 | 5 | 5 | 5 |
|   | 5 | 0 | 5 | 5 | 5 | 5 | 5 | 5 | 5 | 5 |
| 7 | 20 | 0 | 3 | 2 | 3 | 5 | 5 | 5 | 5 | 4 |
|   | 10 | 0 | 2 | 1 | 2 | 4 | 5 | 5 | 5 | 3 |
|   | 5 | 0 | 1 | 0 | 1 | 2 | 5 | 5 | 5 | 2 |
| 8 | 20 | 0 | 5 | 4 | 3 | 5 | 5 | 5 | 5 | 4 |
|   | 10 | 0 | 4 | 3 | 2 | 5 | 5 | 5 | 5 | 3 |
|   | 5 | 0 | 2 | 2 | 1 | 4 | 5 | 5 | 5 | 2 |
| 9 | 20 | 0 | 5 | 5 | 5 | 5 | 5 | 5 | 5 | 5 |
|   | 10 | 0 | 5 | 5 | 5 | 5 | 5 | 5 | 5 | 5 |
|   | 5 | 0 | 5 | 5 | 5 | 5 | 5 | 5 | 5 | 5 |
| 10 | 20 | 0 | 5 | 4 | 4 | 5 | 5 | 5 | 5 | 5 |
|   | 10 | 0 | 4 | 3 | 3 | 4 | 5 | 5 | 5 | 3 |
|   | 5 | 0 | 2 | 2 | 1 | 2 | 5 | 5 | 5 | 2 |
| 11 | 20 | 0 | 5 | 5 | 5 | 5 | 5 | 5 | 5 | 5 |
|   | 10 | 0 | 5 | 5 | 5 | 5 | 5 | 5 | 5 | 5 |
|   | 5 | 0 | 5 | 5 | 5 | 5 | 5 | 5 | 5 | 5 |
| 12 | 20 | 0 | 5 | 4 | 3 | 4 | 5 | 5 | 5 | 4 |
|   | 10 | 0 | 4 | 3 | 3 | 3 | 5 | 5 | 5 | 3 |
|   | 5 | 0 | 3 | 2 | 1 | 2 | 5 | 5 | 5 | 2 |
| 13 | 20 | 0 | 5 | 4 | 3 | 5 | 5 | 5 | 5 | 4 |
|   | 10 | 0 | 4 | 3 | 3 | 4 | 5 | 5 | 5 | 2 |
|   | 5 | 0 | 3 | 2 | 1 | 2 | 5 | 5 | 5 | 1 |
| 14 | 20 | 0 | 5 | 5 | 5 | 5 | 5 | 5 | 5 | 5 |
|   | 10 | 0 | 5 | 5 | 5 | 5 | 5 | 5 | 5 | 5 |
|   | 5 | 0 | 5 | 5 | 5 | 5 | 5 | 5 | 5 | 5 |
| 15 | 20 | 0 | 5 | 4 | 3 | 5 | 5 | 5 | 5 | 4 |
|   | 10 | 0 | 4 | 3 | 2 | 5 | 5 | 5 | 5 | 3 |
|   | 5 | 0 | 3 | 2 | 1 | 4 | 5 | 5 | 5 | 2 |
| 16 | 20 | 0 | 5 | 5 | 5 | 5 | 5 | 5 | 5 | 5 |
|   | 10 | 0 | 5 | 5 | 5 | 5 | 5 | 5 | 5 | 5 |
|   | 5 | 0 | 5 | 5 | 5 | 5 | 5 | 5 | 5 | 5 |
| 17 | 20 | 0 | 3 | 2 | 2 | 3 | 5 | 5 | 5 | 2 |
|   | 10 | 0 | 2 | 1 | 1 | 2 | 5 | 5 | 5 | 2 |
|   | 5 | 0 | 1 | 0 | 0 | 0 | 5 | 5 | 5 | 1 |
| 18 | 20 | 0 | 3 | 2 | 2 | 2 | 5 | 5 | 5 | 2 |
|   | 10 | 0 | 2 | 0 | 1 | 0 | 5 | 5 | 5 | 2 |
|   | 5 | 0 | 1 | 0 | 0 | 0 | 5 | 5 | 5 | 0 |
| 19 | 20 | 0 | 5 | 4 | 3 | 5 | 5 | 5 | 5 | 4 |
|   | 10 | 0 | 5 | 4 | 3 | 5 | 5 | 5 | 5 | 4 |
|   | 5 | 0 | 4 | 3 | 2 | 5 | 5 | 5 | 5 | 3 |
| 20 | 20 | 0 | 5 | 4 | 3 | 5 | 5 | 5 | 5 | 4 |
|   | 10 | 0 | 5 | 4 | 3 | 5 | 5 | 5 | 5 | 4 |
|   | 5 | 0 | 3 | 2 | 1 | 3 | 5 | 5 | 5 | 2 |
| 21 | 20 | 0 | 5 | 4 | 4 | 5 | 5 | 5 | 5 | 4 |
|   | 10 | 0 | 4 | 3 | 2 | 5 | 5 | 5 | 5 | 3 |
|   | 5 | 0 | 3 | 2 | 1 | 3 | 5 | 5 | 5 | 2 |
| 22 | 20 | 0 | 5 | 4 | 4 | 5 | 5 | 5 | 5 | 4 |
|   | 10 | 0 | 4 | 3 | 2 | 5 | 5 | 5 | 5 | 3 |
|   | 5 | 0 | 2 | 2 | 1 | 4 | 5 | 5 | 5 | 1 |
| 23 | 20 | 0 | 4 | 3 | 2 | 4 | 5 | 5 | 5 | 3 |
|   | 10 | 0 | 3 | 2 | 2 | 2 | 5 | 5 | 5 | 2 |
|   | 5 | 0 | 2 | 2 | 0 | 0 | 5 | 5 | 5 | 1 |
| 24 | 20 | 0 | 4 | 3 | 3 | 4 | 5 | 5 | 5 | 3 |
|   | 10 | 0 | 3 | 2 | 2 | 2 | 5 | 5 | 5 | 2 |
|   | 5 | 0 | 2 | 1 | 0 | 0 | 5 | 5 | 5 | 0 |
| 25 | 20 | 0 | 5 | 5 | 5 | 5 | 5 | 5 | 5 | 5 |
|   | 10 | 0 | 5 | 5 | 5 | 5 | 5 | 5 | 5 | 5 |
|   | 5 | 0 | 5 | 5 | 5 | 5 | 5 | 5 | 5 | 5 |
| 26 | 20 | 0 | 5 | 4 | 4 | 5 | 5 | 5 | 5 | 4 |
|   | 10 | 0 | 5 | 3 | 3 | 5 | 5 | 5 | 5 | 4 |
|   | 5 | 0 | 4 | 3 | 2 | 5 | 5 | 5 | 5 | 3 |

TABLE 2-continued

| Test compound No. | Dose g/a | Rice seedlings | Barnyardgrass | Slender spikerush | Flat stage | Scirpus hotarui | Cyperus difformis | Monochoria | Toothcup | Arrowhead |
|---|---|---|---|---|---|---|---|---|---|---|
| 27 | 20 | 0 | 5 | 5 | 5 | 5 | 5 | 5 | 5 | 5 |
|    | 10 | 0 | 5 | 5 | 5 | 5 | 5 | 5 | 5 | 5 |
|    | 5  | 0 | 5 | 5 | 5 | 5 | 5 | 5 | 5 | 5 |
| 28 | 20 | 0 | 5 | 5 | 5 | 5 | 5 | 5 | 5 | 5 |
|    | 10 | 0 | 5 | 5 | 5 | 5 | 5 | 5 | 5 | 5 |
|    | 5  | 0 | 5 | 5 | 5 | 5 | 5 | 5 | 5 | 5 |
| 29 | 20 | 0 | 5 | 5 | 4 | 5 | 5 | 5 | 5 | 4 |
|    | 10 | 0 | 5 | 4 | 3 | 5 | 5 | 5 | 5 | 4 |
|    | 5  | 0 | 4 | 3 | 2 | 4 | 5 | 5 | 5 | 3 |
| 30 | 20 | 0 | 5 | 5 | 4 | 5 | 5 | 5 | 5 | 4 |
|    | 10 | 0 | 5 | 4 | 4 | 5 | 5 | 5 | 5 | 4 |
|    | 5  | 0 | 4 | 3 | 3 | 3 | 5 | 5 | 5 | 3 |
| 31 | 20 | 0 | 5 | 4 | 3 | 5 | 5 | 5 | 5 | 4 |
|    | 10 | 0 | 5 | 4 | 2 | 5 | 5 | 5 | 5 | 4 |
|    | 5  | 0 | 4 | 2 | 1 | 3 | 5 | 5 | 5 | 2 |
| 32 | 20 | 0 | 5 | 5 | 5 | 5 | 5 | 5 | 5 | 5 |
|    | 10 | 0 | 5 | 5 | 5 | 5 | 5 | 5 | 5 | 5 |
|    | 5  | 0 | 5 | 5 | 5 | 5 | 5 | 5 | 5 | 5 |
| 33 | 20 | 0 | 5 | 5 | 5 | 5 | 5 | 5 | 5 | 5 |
|    | 10 | 0 | 5 | 5 | 5 | 5 | 5 | 5 | 5 | 5 |
|    | 5  | 0 | 5 | 5 | 5 | 5 | 5 | 5 | 5 | 5 |
| 34 | 20 | 0 | 5 | 4 | 3 | 5 | 5 | 5 | 5 | 4 |
|    | 10 | 0 | 4 | 3 | 2 | 3 | 5 | 5 | 5 | 3 |
|    | 5  | 0 | 2 | 1 | 1 | 1 | 5 | 5 | 5 | 1 |
| 35 | 20 | 0 | 5 | 4 | 3 | 5 | 5 | 5 | 5 | 4 |
|    | 10 | 0 | 4 | 3 | 2 | 4 | 5 | 5 | 5 | 3 |
|    | 5  | 0 | 3 | 2 | 0 | 2 | 5 | 5 | 5 | 1 |
| 36 | 20 | 0 | 4 | 3 | 2 | 3 | 5 | 5 | 5 | 3 |
|    | 10 | 0 | 2 | 1 | 1 | 2 | 5 | 5 | 5 | 1 |
|    | 5  | 0 | 1 | 0 | 0 | 0 | 5 | 5 | 5 | 0 |
| 37 | 20 | 0 | 5 | 4 | 3 | 5 | 5 | 5 | 5 | 4 |
|    | 10 | 0 | 4 | 3 | 2 | 5 | 5 | 5 | 5 | 3 |
|    | 5  | 0 | 3 | 1 | 1 | 2 | 5 | 5 | 5 | 2 |
| 38 | 20 | 0 | 5 | 5 | 4 | 5 | 5 | 5 | 5 | 5 |
|    | 10 | 0 | 5 | 5 | 3 | 5 | 5 | 5 | 5 | 4 |
|    | 5  | 0 | 5 | 3 | 2 | 5 | 5 | 5 | 5 | 3 |
| 39 | 20 | 0 | 5 | 5 | 4 | 5 | 5 | 5 | 5 | 5 |
|    | 10 | 0 | 5 | 4 | 3 | 5 | 5 | 5 | 5 | 4 |
|    | 5  | 0 | 4 | 3 | 1 | 5 | 5 | 5 | 5 | 2 |
| 40 | 20 | 0 | 5 | 5 | 5 | 5 | 5 | 5 | 5 | 5 |
|    | 10 | 0 | 5 | 5 | 5 | 5 | 5 | 5 | 5 | 5 |
|    | 5  | 0 | 5 | 5 | 5 | 5 | 5 | 5 | 5 | 5 |
| 41 | 20 | 0 | 5 | 4 | 4 | 5 | 5 | 5 | 5 | 4 |
|    | 10 | 0 | 5 | 3 | 3 | 5 | 5 | 5 | 5 | 3 |
|    | 5  | 0 | 4 | 2 | 2 | 4 | 5 | 5 | 5 | 2 |
| 42 | 20 | 0 | 5 | 4 | 4 | 5 | 5 | 5 | 5 | 4 |
|    | 10 | 0 | 5 | 4 | 3 | 4 | 5 | 5 | 5 | 4 |
|    | 5  | 0 | 4 | 3 | 2 | 3 | 5 | 5 | 5 | 3 |
| 43 | 20 | 0 | 5 | 5 | 5 | 5 | 5 | 5 | 5 | 5 |
|    | 10 | 0 | 5 | 5 | 5 | 5 | 5 | 5 | 5 | 5 |
|    | 5  | 0 | 5 | 5 | 5 | 5 | 5 | 5 | 5 | 5 |
| 44 | 20 | 0 | 5 | 5 | 5 | 5 | 5 | 5 | 5 | 5 |
|    | 10 | 0 | 5 | 4 | 3 | 5 | 5 | 5 | 5 | 4 |
|    | 5  | 0 | 5 | 3 | 2 | 5 | 5 | 5 | 5 | 3 |
| 45 | 20 | 0 | 5 | 5 | 5 | 5 | 5 | 5 | 5 | 5 |
|    | 10 | 0 | 5 | 5 | 5 | 5 | 5 | 5 | 5 | 5 |
|    | 5  | 0 | 5 | 5 | 4 | 5 | 5 | 5 | 5 | 4 |

(B) The above test (A) was repeated for the compounds No. 46 through 91, but no seed of *Cyperus difformis* was used in this test and each test compound was applied in dose of 50 g/a.

The results are set forth in the following Table 3, wherein evaluation of herbicidal effects is conducted according to the same rating system as mentioned in test (A).

(C) The above test (A) was also repeated for several compounds as indicated in Table 4 at various doses indicated in said Table, but no seed of *Cyperus difformis* and of Toothcup was used in this test.

The results are shown in the following Table 4, wherein the evaluation follows the same rating system as in test (A).

TABLE 3

| | | | (Dose = 50 g/a) | | | | | |
|---|---|---|---|---|---|---|---|---|
| Test compound No. | Rice seedlings | Barnyardgrass | Scirpus hotarui | Slender spikerush | Flat stage | Monochoria | Toothcup | Arrowhead |
| 46 | 0 | 2 | 2 | 3 | 2 | 5 | 5 | 2 |
| 47 | 0 | 2 | 4 | 4 | 4 | 5 | 5 | 5 |

TABLE 3-continued (Dose = 50 g/a)

| Test compound No. | Rice seedlings | Barnyard-grass | Scirpus hotarui | Slender spikerush | Flatstage | Monochoria | Toothcup | Arrowhead |
|---|---|---|---|---|---|---|---|---|
| 48 | 0 | 2 | 2 | 2 | 1 | 5 | 5 | 1 |
| 49 | 0 | 2 | 3 | 2 | 2 | 5 | 5 | 3 |
| 50 | 0 | 2 | 4 | 2 | 2 | 5 | 5 | 2 |
| 51 | 0 | 2 | 3 | 1 | 1 | 5 | 5 | 2 |
| 52 | 0 | 5 | 3 | 2 | 5 | 5 | 5 | 3 |
| 53 | 0 | 5 | 5 | 5 | 5 | 5 | 5 | 5 |
| 54 | 0 | 5 | 5 | 5 | 5 | 5 | 5 | 5 |
| 55 | 0 | 5 | 5 | 5 | 5 | 5 | 5 | 5 |
| 56 | 0 | 5 | 5 | 5 | 5 | 5 | 5 | 5 |
| 57 | 0 | 5 | 5 | 5 | 5 | 5 | 5 | 5 |
| 58 | 0 | 5 | 5 | 5 | 5 | 5 | 5 | 5 |
| 59 | 0 | 5 | 3 | 3 | 4 | 5 | 5 | 3 |
| 60 | 0 | 4 | 2 | 2 | 2 | 5 | 5 | 2 |
| 61 | 0 | 5 | 3 | 3 | 5 | 5 | 5 | 2 |
| 62 | 0 | 5 | 2 | 3 | 5 | 5 | 5 | 5 |
| 63 | 0 | 4 | 5 | 3 | 3 | 5 | 5 | 2 |
| 64 | 0 | 3 | 3 | 3 | 2 | 5 | 5 | 2 |
| 65 | 0 | 5 | 5 | 3 | 2 | 5 | 5 | 5 |
| 66 | 0 | 5 | 5 | 4 | 5 | 5 | 5 | 3 |
| 67 | 0 | 5 | 4 | 3 | 4 | 5 | 5 | 2 |
| 68 | 0 | 5 | 5 | 2 | 4 | 5 | 5 | 2 |
| 69 | 0 | 4 | 2 | 2 | 2 | 5 | 5 | 2 |
| 70 | 0 | 3 | 5 | 2 | 2 | 5 | 5 | 2 |
| 71 | 0 | 4 | 4 | 4 | 3 | 5 | 5 | 2 |
| 72 | 0 | 4 | 4 | 3 | 4 | 5 | 5 | 2 |
| 73 | 0 | 4 | 4 | 3 | 5 | 5 | 5 | 2 |
| 74 | 0 | 3 | 4 | 3 | 4 | 5 | 5 | 2 |
| 75 | 0 | 5 | 5 | 4 | 5 | 5 | 5 | 5 |
| 76 | 0 | 5 | 5 | 5 | 5 | 5 | 5 | 5 |
| 77 | 0 | 5 | 5 | 5 | 5 | 5 | 5 | 5 |
| 78 | 0 | 5 | 5 | 5 | 5 | 5 | 5 | 5 |
| 79 | 0 | 5 | 5 | 5 | 5 | 5 | 5 | 5 |
| 80 | 0 | 5 | 5 | 5 | 5 | 5 | 5 | 5 |
| 81 | 0 | 5 | 5 | 5 | 5 | 5 | 5 | 5 |
| 82 | 0 | 5 | 5 | 5 | 5 | 5 | 5 | 5 |
| 83 | 0 | 5 | 5 | 5 | 5 | 5 | 5 | 5 |
| 84 | 0 | 5 | 4 | 4 | 4 | 5 | 5 | 4 |
| 85 | 0 | 5 | 5 | 4 | 5 | 5 | 5 | 5 |
| 86 | 0 | 5 | 5 | 3 | 5 | 5 | 5 | 5 |
| 87 | 0 | 4 | 3 | 3 | 5 | 5 | 5 | 4 |
| 88 | 0 | 5 | 5 | 3 | 5 | 5 | 5 | 5 |
| 89 | 0 | 3 | 2 | 2 | 4 | 5 | 5 | 2 |
| 90 | 0 | 2 | 4 | 2 | 2 | 5 | 5 | 3 |
| 91 | 0 | 2 | 3 | 2 | 4 | 5 | 5 | 4 |

TABLE 4

| Test compound No. | Dose g/a | Rice seedlings | Barnyard-grass | Scirpus hotarui | Slender spikerush | Flatstage | Monochoria | Arrowhead |
|---|---|---|---|---|---|---|---|---|
| 76 | 20 | 0 | 5 | 5 | 5 | 5 | 5 | 5 |
|    | 10 | 0 | 5 | 5 | 5 | 5 | 5 | 5 |
|    | 5  | 0 | 5 | 5 | 5 | 4 | 5 | 5 |
|    | 2.5| 0 | 5 | 5 | 4 | 3 | 5 | 4 |
| 77 | 20 | 0 | 5 | 5 | 5 | 5 | 5 | 5 |
|    | 10 | 0 | 5 | 5 | 5 | 5 | 5 | 5 |
|    | 5  | 0 | 5 | 5 | 5 | 4 | 5 | 5 |
|    | 2.5| 0 | 5 | 5 | 4 | 3 | 5 | 3 |
| 79 | 20 | 0 | 5 | 5 | 5 | 5 | 5 | 5 |
|    | 10 | 0 | 5 | 5 | 5 | 5 | 5 | 5 |
|    | 5  | 0 | 5 | 5 | 5 | 5 | 5 | 5 |
|    | 2.5| 0 | 5 | 5 | 5 | 5 | 5 | 5 |
| Nitrofen | 20 | 1 | 5 | 5 | 4 | 3 | 5 | 2 |
|          | 10 | 0 | 4 | 4 | 2 | 2 | 5 | 1 |
|          | 5  | 0 | 3 | 2 | 1 | 0 | 5 | 0 |
|          | 2.5| 0 | 2 | 1 | 0 | 0 | 3 | 0 |

Nitrofen: 2,4-dichloro-4'-nitrodiphenyl ether

EXPERIMENT 2

Tests against barnyard-grass at various growth stages

Beaker pots, each having the surface of 1/5000 are, were packed with Ube soil and seeds of barnyard-grass were sowed thereover for the growth to 0.5 leaf, 1.0 leaf and 1.5 leaf stages and then the pots were filled with water to a depth of 3 cm.

Each test compound at the indicated dose was applied dropwise with a pipette. Then, the pots were kept in a glass chamber at an average temperature of approximately 25° C.

After 3 weeks from the treatment, herbicidal effects of each test compound were investigated.

The results are summarized in Table 5 wherein the same rating system as in the Experiment 1 was applied.

TABLE 5

| Test Compound No. | Dose g/a | 0.5 leaf | 1.0 leaf | 1.5 leaf |
|---|---|---|---|---|
| 25 | 20 | 5 | 5 | 5 |
|    | 10 | 5 | 5 | 4 |
|    | 5  | 5 | 5 | 3 |
| 27 | 20 | 5 | 5 | 5 |
|    | 10 | 5 | 5 | 5 |
|    | 5  | 5 | 5 | 4 |
| 33 | 20 | 5 | 5 | 5 |
|    | 10 | 5 | 5 | 5 |
|    | 5  | 5 | 5 | 5 |
| 40 | 20 | 5 | 5 | 5 |
|    | 10 | 5 | 5 | 5 |
|    | 5  | 5 | 5 | 4 |

TABLE 5-continued

| Test Compound No. | Dose g/a | Treatment stage | | |
|---|---|---|---|---|
| | | 0.5 leaf | 1.0 leaf | 1.5 leaf |
| 43 | 20 | 5 | 5 | 5 |
| | 10 | 5 | 5 | 4 |
| | 5 | 5 | 5 | 2 |

EXPERIMENT 3

Soil treatment tests for upland weed control (A) Wagner pots, each having the surface of 1/5000 are, were packed with Ube soil and then seeds of corn (variety: Golden-cross bantam), of soybean (variety: Syuho), of Japanese radish (variety: Mino-wase), of large crabgrass, of green foxtail, of liuid amaranth, of common lambsquarters, of smartweed and of common purslane were sowed. After covering with soil, each test compound was sprayed under pressure onto the soil surface at the indicated dose and the pots were kept in a glass chamber at an average temperature of approximately 25° C.

After 3 weeks from the treatment, herbicidal effects of each test compound were investigated to give the results as shown in Table 6, wherein the same rating system as in the Experiment 1 was applied.

(B) The above test (A) was repeated for the compounds indicated in Table 7 at the dose of 50 g/a, but seeds of large crabgrass, of water foxtail, of white clover, of common lambsquarters, of common purslane and of "Gishigishi" (*Rumex japonicus*) were used in this test.

Table 7 shows the results obtained, using the same evaluation system as described in Experiment 1.

TABLE 6

| Test compound No. | Dose g/a | Corn | Soybean | Japanese radish | Large crabgrass | Green foxtail | Liquid amaranth | Common lambsquarters | Smartweed | Common purslane |
|---|---|---|---|---|---|---|---|---|---|---|
| 9 | 20 | 0 | 0 | 0 | 5 | 3 | 5 | 5 | 5 | 5 |
|   | 10 | 0 | 0 | 0 | 5 | 2 | 5 | 5 | 5 | 5 |
|   | 5  | 0 | 0 | 0 | 5 | 1 | 5 | 5 | 5 | 5 |
| 11 | 20 | 0 | 0 | 0 | 5 | 3 | 5 | 5 | 5 | 5 |
|    | 10 | 0 | 0 | 0 | 5 | 2 | 5 | 5 | 5 | 5 |
|    | 5  | 0 | 0 | 0 | 5 | 2 | 5 | 5 | 5 | 5 |
| 14 | 20 | 0 | 0 | 0 | 5 | 4 | 5 | 5 | 5 | 5 |
|    | 10 | 0 | 0 | 0 | 5 | 2 | 5 | 5 | 5 | 5 |
|    | 5  | 0 | 0 | 0 | 5 | 1 | 5 | 5 | 5 | 5 |
| 16 | 20 | 0 | 0 | 0 | 5 | 4 | 5 | 5 | 5 | 5 |
|    | 10 | 0 | 0 | 0 | 5 | 3 | 5 | 5 | 5 | 5 |
|    | 5  | 0 | 0 | 0 | 5 | 2 | 5 | 5 | 5 | 5 |
| 25 | 20 | 0 | 0 | 0 | 5 | 4 | 5 | 5 | 5 | 5 |
|    | 10 | 0 | 0 | 0 | 5 | 3 | 5 | 5 | 5 | 5 |
|    | 5  | 0 | 0 | 0 | 5 | 2 | 5 | 5 | 5 | 5 |
| 27 | 20 | 0 | 0 | 0 | 5 | 5 | 5 | 5 | 5 | 5 |
|    | 10 | 0 | 0 | 0 | 5 | 5 | 5 | 5 | 5 | 5 |
|    | 5  | 0 | 0 | 0 | 5 | 5 | 5 | 5 | 5 | 5 |
| 28 | 20 | 0 | 0 | 0 | 5 | 5 | 5 | 5 | 5 | 5 |
|    | 10 | 0 | 0 | 0 | 5 | 4 | 5 | 5 | 5 | 5 |
|    | 5  | 0 | 0 | 0 | 5 | 3 | 5 | 5 | 5 | 5 |
| 32 | 20 | 0 | 0 | 0 | 5 | 4 | 5 | 5 | 5 | 5 |
|    | 10 | 0 | 0 | 0 | 5 | 3 | 5 | 5 | 5 | 5 |
|    | 5  | 0 | 0 | 0 | 5 | 3 | 5 | 5 | 5 | 5 |
| 33 | 20 | 0 | 0 | 0 | 5 | 5 | 5 | 5 | 5 | 5 |
|    | 10 | 0 | 0 | 0 | 5 | 5 | 5 | 5 | 5 | 5 |
|    | 5  | 0 | 0 | 0 | 5 | 5 | 5 | 5 | 5 | 5 |
| 40 | 20 | 0 | 0 | 0 | 5 | 5 | 5 | 5 | 5 | 5 |
|    | 10 | 0 | 0 | 0 | 5 | 5 | 5 | 5 | 5 | 5 |
|    | 5  | 0 | 0 | 0 | 5 | 5 | 5 | 5 | 5 | 5 |
| 43 | 20 | 0 | 0 | 0 | 5 | 5 | 5 | 5 | 5 | 5 |
|    | 10 | 0 | 0 | 0 | 5 | 5 | 5 | 5 | 5 | 5 |
|    | 5  | 0 | 0 | 0 | 5 | 5 | 5 | 5 | 5 | 5 |
| 45 | 20 | 0 | 0 | 0 | 5 | 5 | 5 | 5 | 5 | 5 |
|    | 10 | 0 | 0 | 0 | 5 | 4 | 5 | 5 | 5 | 5 |
|    | 5  | 0 | 0 | 0 | 5 | 3 | 5 | 5 | 5 | 5 |
| 76 | 20 | 0 | 0 | 0 | 5 | 5 | 5 | 5 | — | 5 |
|    | 10 | 0 | 0 | 0 | 5 | 5 | 5 | 5 |   | 5 |
|    | 5  | 0 | 0 | 0 | 5 | 5 | 5 | 5 |   | 5 |
| 77 | 20 | 0 | 0 | 0 | 5 | 5 | 5 | 5 | — | 5 |
|    | 10 | 0 | 0 | 0 | 5 | 5 | 5 | 5 |   | 5 |
|    | 5  | 0 | 0 | 0 | 5 | 5 | 5 | 5 |   | 5 |
| 79 | 20 | 0 | 0 | 0 | 5 | 5 | 5 | 5 | — | 5 |
|    | 10 | 0 | 0 | 0 | 5 | 5 | 5 | 5 |   | 5 |
|    | 5  | 0 | 0 | 0 | 5 | 5 | 5 | 5 |   | 5 |
| 82 | 20 | 0 | 0 | 0 | 5 | 5 | 5 | 5 | — | 5 |
|    | 10 | 0 | 0 | 0 | 5 | 5 | 5 | 5 |   | 5 |
|    | 5  | 0 | 0 | 0 | 5 | 4 | 5 | 5 |   | 5 |
| 83 | 20 | 0 | 0 | 0 | 5 | 5 | 5 | 5 | — | 5 |
|    | 10 | 0 | 0 | 0 | 5 | 4 | 5 | 5 |   | 5 |
|    | 5  | 0 | 0 | 0 | 4 | 3 | 5 | 5 |   | 5 |
| Nitrofen | 20 | 0 | 0 | 0 | 2 | 2 | 5 | 5 | — | 5 |
|          | 10 | 0 | 0 | 0 | 1 | 0 | 5 | 4 |   | 5 |
|          | 5  | 0 | 0 | 0 | 0 | 0 | 4 | 3 |   | 4 |

TABLE 7

| Test compound No. | Large-crabgrass | Water foxtail | White clover | Common lambsquarters | Common purslane | Rumex japonicus |
|---|---|---|---|---|---|---|
| 52 | 3 | 2 | 3 | 5 | 4 | 5 |
| 53 | 4 | 5 | 2 | 5 | 5 | 5 |
| 54 | 3 | 2 | 3 | 5 | 3 | 3 |
| 55 | 2 | 2 | 3 | 4 | 4 | 3 |
| 56 | 2 | 2 | 3 | 2 | 5 | 2 |
| 57 | 3 | 2 | 4 | 3 | 5 | 4 |
| 58 | 4 | 5 | 2 | 5 | 5 | 5 |
| 61 | 4 | 4 | 3 | 4 | 5 | 5 |
| 62 | 4 | 4 | 2 | 5 | 5 | 5 |
| 65 | 5 | 3 | 5 | 5 | 4 | 4 |
| 67 | 3 | 2 | 2 | 5 | 5 | 2 |
| 75 | 4 | 4 | 5 | 5 | 5 | 5 |
| 76 | 5 | 5 | 5 | 5 | 5 | 5 |
| 77 | 5 | 5 | 5 | 5 | 5 | 5 |
| 78 | 5 | 5 | 5 | 5 | 5 | 5 |
| 79 | 5 | 5 | 5 | 5 | 5 | 5 |
| 80 | 5 | 5 | 5 | 5 | 5 | 5 |
| 81 | 5 | 5 | 5 | 5 | 5 | 5 |
| 82 | 5 | 5 | 5 | 5 | 5 | 5 |
| 83 | 5 | 5 | 5 | 5 | 5 | 5 |
| 88 | 4 | 4 | 2 | 5 | 5 | 4 |
| 89 | 3 | 3 | 2 | 5 | 5 | 3 |
| 90 | 2 | 2 | 2 | 5 | 4 | 2 |

EXPERIMENT 4

Foliar treatment tests for upland weed control (A) Wagner pots, each having the surface of 1/5000 are, were packed with Ube soil and large crabgrass, common lambsquarters and smartweed were grown therein.

Then, a wettable powder of each test compound was diluted with water containing 100 ppm of "Neoesterin" (trade name of spreader available from Toa Noyaku K.K.) to a concentration of the active ingredient of 0.5 wt.% and the resulting preparation was uniformly applied to seedlings by foliar spraying under pressure at a dose of 5 ml. per pot. Then, the pots were kept in a glass chamber at an average temperature of approximately 25° C.

After 3 weeks from the treatment, herbicidal effects of each test compound were investigated.

The results are summarized in Table 8 wherein the same rating systems as in the Experiment 1 were applied.

(B) Using the same Wagner pots as in test (A), seedlings of large crabgrass at 3 leaf stage, of common lambsquarters at 2 leaf stage, of smartweed at 2 leaf stage and of purple nutsedge at 4 leaf stage were planted and grown.

The herbicidal treatment was conducted in the same manner as in test (A) to give the results as shown in Table 9, wherein the same rating system as used in Experiment 1 was applied.

TABLE 8

| Test compound No. | Large crabgrass | Common lambsquarters | Smartweed |
|---|---|---|---|
| 6 | 5 | 5 | 5 |
| 9 | 5 | 5 | 5 |
| 11 | 5 | 5 | 5 |
| 14 | 5 | 5 | 5 |
| 16 | 5 | 5 | 5 |
| 25 | 5 | 5 | 5 |
| 27 | 5 | 5 | 5 |
| 28 | 5 | 5 | 5 |
| 32 | 5 | 5 | 5 |
| 33 | 5 | 5 | 5 |
| 40 | 5 | 5 | 5 |
| 43 | 5 | 5 | 5 |

TABLE 9

| Test compound No. | Large crabgrass | Common lambsquarters | Smartweed | Purple nutsedge |
|---|---|---|---|---|
| 54 | 4 | 5 | 5 | 2 |
| 58 | 3 | 5 | 5 | 2 |
| 65 | 5 | 5 | 5 | 3 |
| 67 | 3 | 5 | 5 | 2 |
| 75 | 5 | 5 | 5 | 3 |
| 76 | 5 | 5 | 5 | 5 |
| 77 | 5 | 5 | 5 | 5 |
| 78 | 5 | 5 | 5 | 5 |
| 79 | 5 | 5 | 5 | 5 |
| 80 | 5 | 5 | 5 | 5 |
| 81 | 5 | 5 | 5 | 5 |
| 82 | 5 | 5 | 5 | 5 |
| 83 | 5 | 5 | 5 | 5 |

What we claim is:

1. A herbicidal composition which comprises (i) a herbicidal carrier and (ii) a herbicidally effective amount of a compound of the formula (I):

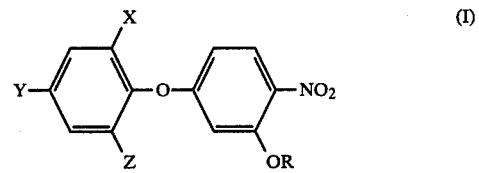

wherein X is a halogen atom; Z is a hydrogen atom or a halogen atom; Y is a halogen atom or a trifluoromethyl group; and R is a group of the formula:

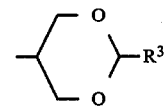

in which $R^3$ is a hydrogen atom or a methyl group.

2. A herbicidal composition according to claim 1, wherein Z is a hydrogen atom.

3. A herbicidal composition according to claim 1, wherein X, Y and Z are all halogen atoms.

4. A herbicidal composition according to claim 1, wherein $R^3$ is a hydrogen atom.

5. A herbicidal composition according to claim 1, wherein the compound (I) is 2-chloro-4-trifluoromethyl-3'-(1,3-dioxa-5-cyclohexyloxy)-4'-nitrodiphenyl ether.

6. A herbicidal composition according to claim 1, wherein the compound (I) is 2-chloro-4-trifluoromethyl-3'-(1,3-dioxa-2-methyl-5-cyclohexyloxy)-4'-nitrodiphenyl ether.

7. A herbicidal composition according to claim 1, wherein the compound (I) is 2,4-dichloro-6-fluoro-3'-(1,3-dioxa-5-cyclohexyloxy)-4'-nitrodiphenyl ether.

8. A novel diphenyl ether derivative represented by the formula (I):

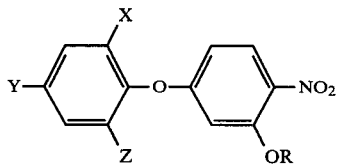 (I)

wherein X is a halogen atom; Z is a hydrogen atom or a halogen atom; Y is a halogen atom or a trifluoromethyl group; and R is a group of the formula:

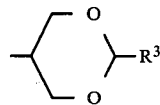

in which $R^3$ is a hydrogen atom or a methyl group.

9. A diphenyl ether derivative according to claim 8, wherein Z is a hydrogen atom.

10. A diphenyl ether derivative according to claim 8, wherein X, Y and Z are all halogen atoms.

11. A diphenyl ether derivative according to claim 8, wherein $R^3$ is a hydrogen atom.

12. A diphenyl ether derivative according to claim 8, namely 2-chloro-4-trifluoromethyl-3'-(1,3-dioxa-5-cyclohexyloxy)-4'-nitrodiphenyl ether.

13. A diphenyl ether derivative according to claim 8, namely 2-chloro-4-trifluoromethyl-3'-(1,3-dioxa-2-methyl-5-cyclohexyloxy)-4'-nitrodiphenyl ether.

14. A diphenyl ether derivative according to claim 8, namely 2,4-dichloro-6-fluoro-3'-(1,3-dioxa-5-cyclohexyloxy)-4'-nitrodiphenyl ether.

* * * * *